(12) United States Patent
Goel et al.

(10) Patent No.: US 10,937,539 B1
(45) Date of Patent: Mar. 2, 2021

(54) AUTOMATED ACTIVITY SUGGESTIONS BASED ON WEARABLE CONNECTIVITY WITH VEHICLE SYSTEMS

(71) Applicant: TOYOTA MOTOR NORTH AMERICA, INC., Plano, TX (US)

(72) Inventors: Ruchin Goel, Plano, TX (US); Ronnie S. Cooke, Allen, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 0 days.

(21) Appl. No.: 16/536,106

(22) Filed: Aug. 8, 2019

(51) Int. Cl.
  *G16H 20/30* (2018.01)
  *G06F 1/16* (2006.01)
  *A61B 5/11* (2006.01)
  *A61B 5/145* (2006.01)
  *A61B 5/0205* (2006.01)
  *A61B 5/024* (2006.01)

(52) U.S. Cl.
  CPC .......... *G16H 20/30* (2018.01); *A61B 5/0205* (2013.01); *A61B 5/1118* (2013.01); *A61B 5/14532* (2013.01); *G06F 1/163* (2013.01); *A61B 5/024* (2013.01)

(58) Field of Classification Search
  CPC ..... G16H 20/30; A61B 5/0205; A61B 5/1118; A61B 5/14532; A61B 5/024; G06F 1/163
  See application file for complete search history.

(56) References Cited

U.S. PATENT DOCUMENTS

| | | | |
|---|---|---|---|
| 9,371,002 B2 * | 6/2016 | Braunberger | B60K 31/00 |
| 9,481,326 B2 | 11/2016 | Chatterjee | |
| 9,868,385 B2 * | 1/2018 | Braunberger | B60Q 1/442 |
| 10,195,901 B2 | 2/2019 | Briggs | |
| 10,220,765 B2 * | 3/2019 | Braunberger | B60Q 1/08 |
| 2008/0015778 A1 * | 1/2008 | Matsuura | G08G 1/167 |
| | | | 701/301 |
| 2008/0297336 A1 * | 12/2008 | Lee | H04L 67/04 |
| | | | 340/439 |
| 2009/0203498 A1 * | 8/2009 | Lingman | B60T 17/221 |
| | | | 477/183 |
| 2012/0078509 A1 * | 3/2012 | Choi | G01C 21/3415 |
| | | | 701/423 |
| 2013/0009761 A1 * | 1/2013 | Horseman | A61B 5/1114 |
| | | | 340/425.5 |
| 2013/0141231 A1 * | 6/2013 | Aberizk | B60T 7/10 |
| | | | 340/467 |
| 2015/0061492 A1 * | 3/2015 | Braunberger | B60K 31/00 |
| | | | 315/82 |
| 2015/0362997 A1 * | 12/2015 | Hatton | G06F 3/017 |
| | | | 701/2 |

(Continued)

FOREIGN PATENT DOCUMENTS

| | | |
|---|---|---|
| CN | 109532490 | 3/2019 |
| DE | 202018100012 | 5/2018 |
| WO | 2016162103 | 10/2016 |

*Primary Examiner* — Rufus C Point

(74) *Attorney, Agent, or Firm* — Sheppard, Mullin, Richter & Hampton LLP; Hector A. Agdeppa; Daniel N. Yannuzzi

(57) ABSTRACT

Systems and methods are provided for automated activity suggestions based on wearable connectivity with vehicle systems. An example method includes collecting health data for an occupant of the vehicle from a wearable device worn by the occupant; determining a location of the vehicle; and suggesting an activity for the occupant based on the collected health data and the location of the vehicle.

19 Claims, 6 Drawing Sheets

(56) References Cited

U.S. PATENT DOCUMENTS

| | | | |
|---|---|---|---|
| 2016/0358477 A1* | 12/2016 | Ansari | G06Q 30/0251 |
| 2017/0151930 A1* | 6/2017 | Boesen | G07C 9/00896 |
| 2017/0151957 A1* | 6/2017 | Boesen | A61B 5/14532 |
| 2017/0153636 A1* | 6/2017 | Boesen | G06F 1/163 |
| 2017/0238174 A1* | 8/2017 | Cech | H04W 12/0605 |
| | | | 455/411 |
| 2017/0240186 A1* | 8/2017 | Hatano | B60W 30/09 |
| 2018/0037224 A1* | 2/2018 | Bogner | B60W 10/20 |
| 2019/0054928 A1* | 2/2019 | Hatano | B60W 60/0057 |
| 2019/0071098 A1* | 3/2019 | Asakura | B60W 30/025 |
| 2020/0027353 A1* | 1/2020 | Takahashi | B60W 50/16 |

* cited by examiner

US 10,937,539 B1

AUTOMATED ACTIVITY SUGGESTIONS BASED ON WEARABLE CONNECTIVITY WITH VEHICLE SYSTEMS

TECHNICAL FIELD

The present disclosure relates generally to vehicles, and in particular, some implementations may relate to providing vehicles that suggest activities based on data collected from wearable devices.

DESCRIPTION OF RELATED ART

Wearable electronic devices are becoming increasingly popular. One class of such devices collects health data from the wearer. For example, some wearable electronic devices collect heart rate data, data describing a number of steps the wearer has taken during the day, and the like. Some of these devices include transmitters for wirelessly sharing collected health data.

At the same time, vehicle computing systems are becoming increasingly sophisticated. Such systems often include transceivers for wirelessly connecting with other electronic devices. Many such vehicles include comprehensive user interfaces for interacting with occupants of the vehicles.

BRIEF SUMMARY OF THE DISCLOSURE

Various embodiments of the disclosed technology provide automated activity suggestions based on wearable connectivity with vehicle systems. In general, one aspect disclosed features vehicle, comprising: a hardware processor; and a non-transitory machine-readable storage medium encoded with instructions executable by the hardware processor to perform a method comprising: collecting health data for an occupant of the vehicle from a wearable device worn by the occupant; determining a location of the vehicle; and suggesting an activity for the occupant based on the collected health data and the location of the vehicle.

Embodiments of the vehicle may include one or more of the following features. In some embodiments, the method further comprises: suggesting a location for the activity. In some embodiments, the method further comprises: collecting weather data; and suggesting the activity for the occupant based on the collected health data, the location of the vehicle, and the weather data. In some embodiments, the method further comprises: collecting a history of activities performed by the occupant; and suggesting the activity for the occupant based on the collected health data, the location of the vehicle, and the history of activities. In some embodiments, the method further comprises: comparing the collected health data to a threshold; and suggesting the activity for the occupant based on the collected health data and the threshold. In some embodiments, collecting the health data for the occupant of the vehicle from the wearable device worn by the occupant comprises: collecting the health directly from the wearable device. In some embodiments, collecting the health data for the occupant of the vehicle from the wearable device worn by the occupant comprises: collecting the health from a portable computing device in communication with the wearable device.

In general, one aspect disclosed features a non-transitory machine-readable storage medium encoded with instructions executable by the hardware processor to perform a method comprising: collecting health data for an occupant of the vehicle from a wearable device worn by the occupant; determining a location of the vehicle; and suggesting an activity for the occupant based on the collected health data and the location of the vehicle.

Embodiments of the medium may include one or more of the following features. In some embodiments, the method further comprises: suggesting a location for the activity. In some embodiments, the method further comprises: collecting weather data; and suggesting the activity for the occupant based on the collected health data, the location of the vehicle, and the weather data. In some embodiments, the method further comprises: collecting a history of activities performed by the occupant; and suggesting the activity for the occupant based on the collected health data, the location of the vehicle, and the history of activities. In some embodiments, the method further comprises: comparing the collected health data to a threshold; and suggesting the activity for the occupant based on the collected health data and the threshold. In some embodiments, collecting the health data for the occupant of the vehicle from the wearable device worn by the occupant comprises: collecting the health directly from the wearable device. In some embodiments, collecting the health data for the occupant of the vehicle from the wearable device worn by the occupant comprises: collecting the health from a portable competing device in communication with the wearable device.

In general, one aspect disclosed features a method for a vehicle, the method comprising: collecting health data for an occupant of the vehicle from a wearable device worn by the occupant; determining a location of the vehicle; and suggesting an activity for the occupant based on the collected health data and the location of the vehicle.

Embodiments of the method may include one or more of the following features. Some embodiments comprise suggesting a location for the activity. Some embodiments comprise collecting weather data; and suggesting the activity for the occupant based on the collected health data, the location of the vehicle, and the weather data. Some embodiments comprise collecting a history of activities performed by the occupant; and suggesting the activity for the occupant based on the collected health data, the location of the vehicle, and the history of activities. Some embodiments comprise comparing the collected health data to a threshold; and suggesting the activity for the occupant based on the collected health data and the threshold. In some embodiments, collecting the health data for the occupant of the vehicle from the wearable device worn by the occupant comprises: collecting the health directly from the wearable device.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

Embodiments of the systems and methods disclosed herein can provide vehicles that communicate with wearable electronic devices to collect health data, and to suggest activities to wearers of the wearable electronic devices based on the collected health data. For example, the health data may include the number of steps the wearer has taken during the day, and the vehicle may suggest the wearer stop the vehicle and take a walk.

In some embodiments, when suggesting the activity, the vehicle may consider the location of the vehicle. For example, the vehicle may identify a park near the vehicle's location, and may suggest the wearer take a walk at that park. The system may also be configured such that the vehicle determines directions to the park and provides those directions to the wearer such as on a turn-by-turn navigation system.

In some embodiments, when suggesting the activity, the vehicle may consider weather conditions. For example, when it is raining, the vehicle may identify an indoor gym near the vehicle, and may suggest the wearer exercise at the gym rather than taking a walk at the park. Again, the system may be configured to determine directions to the facility and provide directions to the wearer to assist the wearer in navigating to the facility.

In some embodiments, when suggesting the activity, the vehicle may consider activities the wearer has performed previously. In such embodiments, the vehicle may store a history of the wearer's activities. For example, the vehicle may suggest the wearer visit a gym the wearer has visited previously.

In some embodiments, when suggesting the activity, the vehicle may consider a health data threshold. In such embodiments, the health data threshold may represent a health or exercise goal of the wearer. For example, the threshold may represent a minimum number of steps the wearer should take during a day. In this example, the vehicle may suggest the wearer take a walk when the number of steps taken by the wearer during the day falls below the threshold number of steps.

In some embodiments, the vehicle may communicate directly with the wearable electronic device to obtain the health data. In other embodiments, the health data may be collected by a portable electronic device, such as a smart phone or the like. In such embodiments, the vehicle may communicate with the portable electronic device to obtain the health data.

Figure 1:
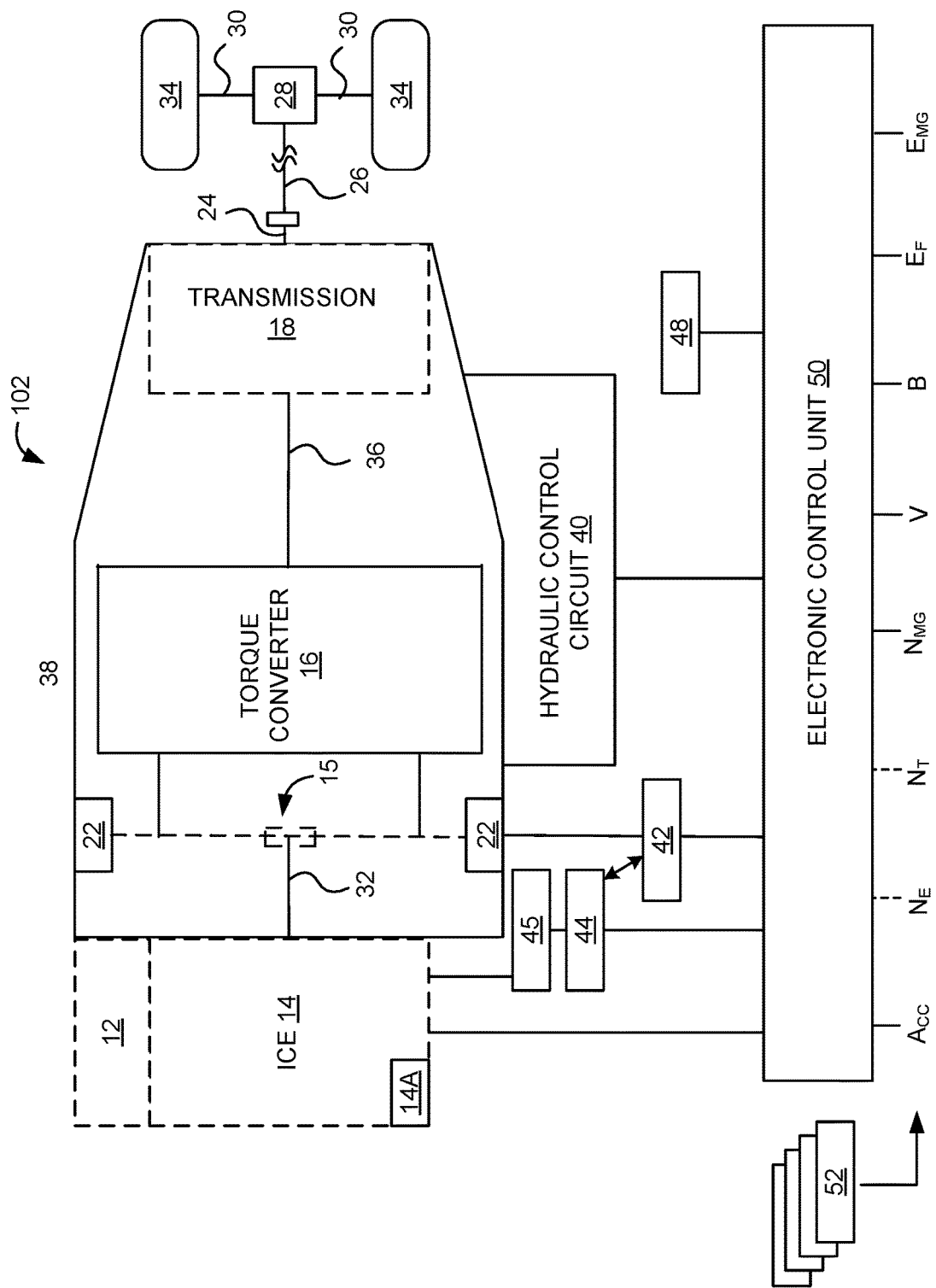
FIG. 1 is a schematic representation of an example hybrid vehicle with which embodiments of the systems and methods disclosed herein may be implemented.

The systems and methods disclosed herein may be implemented with any of a number of different vehicles and vehicle types. For example, the systems and methods disclosed herein may be used with automobiles, trucks, motorcycles, recreational vehicles and other like on-or off-road vehicles. In addition, the principals disclosed herein may also extend to other vehicle types as well. An example hybrid electric vehicle (HEV) in which embodiments of the disclosed technology may be implemented is illustrated in FIG. 1. Although the example described with reference to FIG. 1 is a hybrid type of vehicle, the systems and methods described herein may be implemented in other types of vehicle including gasoline- or diesel-powered vehicles, fuel-cell vehicles, electric vehicles, or other vehicles.

FIG. 1 illustrates a drive system of a vehicle 102 that may include an internal combustion engine 14 and one or more electric motors 22 (which may also serve as generators) as sources of motive power. Driving force generated by the internal combustion engine 14 and motors 22 can be transmitted to one or more wheels 34 via a torque converter 16, a transmission 18, a differential gear device 28, and a pair of axles 30.

As an HEV, vehicle 102 may be driven/powered with either or both of engine 14 and the motor(s) 22 as the drive source for travel. For example, a first travel mode may be an engine-only travel mode that only uses internal combustion engine 14 as the source of motive power. A second travel mode may be an EV travel mode that only uses the motor(s) 22 as the source of motive power. A third travel mode may be an HEV travel mode that uses engine 14 and the motor(s) 22 as the sources of motive power. In the engine-only and HEV travel modes, vehicle 102 relies on the motive force generated at least by internal combustion engine 14, and a clutch 15 may be included to engage engine 14. In the EV travel mode, vehicle 102 is powered by the motive force generated by motor 22 while engine 14 may be stopped and clutch 15 disengaged.

Engine 14 can be an internal combustion engine such as a gasoline, diesel or similarly powered engine in which fuel is injected into and combusted in a combustion chamber. A cooling system 12 can be provided to cool the engine 14 such as, for example, by removing excess heat from engine 14. For example, cooling system 12 can be implemented to include a radiator, a water pump and a series of cooling channels. In operation, the water pump circulates coolant through the engine 14 to absorb excess heat from the engine. The heated coolant is circulated through the radiator to remove heat from the coolant, and the cold coolant can then be recirculated through the engine. A fan may also be included to increase the cooling capacity of the radiator. The water pump, and in some instances the fan, may operate via a direct or indirect coupling to the driveshaft of engine 14. In other applications, either or both the water pump and the fan may be operated by electric current such as from battery 44.

An output control circuit 14A may be provided to control drive (output torque) of engine 14. Output control circuit 14A may include a throttle actuator to control an electronic throttle valve that controls fuel injection, an ignition device that controls ignition timing, and the like. Output control circuit 14A may execute output control of engine 14 according to a command control signal(s) supplied from an electronic control unit 50, described below. Such output control can include, for example, throttle control, fuel injection control, and ignition timing control.

Motor 22 can also be used to provide motive power in vehicle 102 and is powered electrically via a battery 44. Battery 44 may be implemented as one or more batteries or other power storage devices including, for example, lead-acid batteries, lithium ion batteries, capacitive storage devices, and so on. Battery 44 may be charged by a battery charger 45 that receives energy from internal combustion engine 14. For example, an alternator or generator may be coupled directly or indirectly to a drive shaft of internal combustion engine 14 to generate an electrical current as a result of the operation of internal combustion engine 14. A clutch can be included to engage/disengage the battery charger 45. Battery 44 may also be charged by motor 22 such as, for example, by regenerative braking or by coasting during which time motor 22 operate as generator.

Motor 22 can be powered by battery 44 to generate a motive force to move the vehicle and adjust vehicle speed. Motor 22 can also function as a generator to generate electrical power such as, for example, when coasting or braking. Battery 44 may also be used to power other electrical or electronic systems in the vehicle. Motor 22 may be connected to battery 44 via an inverter 42. Battery 44 can include, for example, one or more batteries, capacitive storage units, or other storage reservoirs suitable for storing electrical energy that can be used to power motor 22. When battery 44 is implemented using one or more batteries, the batteries can include, for example, nickel metal hydride batteries, lithium ion batteries, lead acid batteries, nickel cadmium batteries, lithium ion polymer batteries, and other types of batteries.

An electronic control unit 50 (described below) may be included and may control the electric drive components of the vehicle as well as other vehicle components. For example, electronic control unit 50 may control inverter 42, adjust driving current supplied to motor 22, and adjust the current received from motor 22 during regenerative coasting and breaking. As a more particular example, output torque of the motor 22 can be increased or decreased by electronic control unit 50 through the inverter 42.

A torque converter 16 can be included to control the application of power from engine 14 and motor 22 to transmission 18. Torque converter 16 can include a viscous fluid coupling that transfers rotational power from the motive power source to the driveshaft via the transmission. Torque converter 16 can include a conventional torque converter or a lockup torque converter. In other embodiments, a mechanical clutch can be used in place of torque converter 16.

Clutch 15 can be included to engage and disengage engine 14 from the drivetrain of the vehicle. In the illustrated example, a crankshaft 32, which is an output member of engine 14, may be selectively coupled to the motor 22 and torque converter 16 via clutch 15. Clutch 15 can be implemented as, for example, a multiple disc type hydraulic frictional engagement device whose engagement is controlled by an actuator such as a hydraulic actuator. Clutch 15 may be controlled such that its engagement state is complete engagement, slip engagement, and complete disengagement complete disengagement, depending on the pressure applied to the clutch. For example, a torque capacity of clutch 15 may be controlled according to the hydraulic pressure supplied from a hydraulic control circuit (not illustrated). When clutch 15 is engaged, power transmission is provided in the power transmission path between the crankshaft 32 and torque converter 16. On the other hand, when clutch 15 is disengaged, motive power from engine 14 is not delivered to the torque converter 16. In a slip engagement state, clutch 15 is engaged, and motive power is provided to torque converter 16 according to a torque capacity (transmission torque) of the clutch 15.

As alluded to above, vehicle 102 may include an electronic control unit 50. Electronic control unit 50 may include circuitry to control various aspects of the vehicle operation. Electronic control unit 50 may include, for example, a microcomputer that includes a one or more processing units (e.g., microprocessors), memory storage (e.g., RAM, ROM, etc.), and I/O devices. The processing units of electronic control unit 50, execute instructions stored in memory to control one or more electrical systems or subsystems in the vehicle. Electronic control unit 50 can include a plurality of electronic control units such as, for example, an electronic engine control module, a powertrain control module, a transmission control module, a suspension control module, a body control module, and so on. As a further example, electronic control units can be included to control systems and functions such as doors and door locking, lighting, human-machine interfaces, cruise control, telematics, braking systems (e.g., ABS or ESC), battery management systems, and so on. These various control units can be implemented using two or more separate electronic control units, or using a single electronic control unit.

In the example illustrated in FIG. 1, electronic control unit 50 receives information from a plurality of sensors included in vehicle 102. For example, electronic control unit 50 may receive signals that indicate vehicle operating conditions or characteristics, or signals that can be used to derive vehicle operating conditions or characteristics. These may include, but are not limited to accelerator operation amount, $A_{CC}$, a revolution speed, $N_E$, of internal combustion engine 14 (engine RPM), a rotational speed, $N_{MG}$, of the motor 22 (motor rotational speed), and vehicle speed, $N_V$. These may also include torque converter 16 output, $N_T$ (e.g., output amps indicative of motor output), brake operation amount/pressure, B, battery SOC (i.e., the charged amount for battery 44 detected by an SOC sensor). Accordingly, vehicle 102 can include a plurality of sensors 52 that can be used to detect various conditions internal or external to the vehicle and provide sensed conditions to engine control unit 50 (which, again, may be implemented as one or a plurality of individual control circuits). In one embodiment, sensors 52 may be included to detect one or more conditions directly or indirectly such as, for example, fuel efficiency, $E_F$, motor efficiency, $E_{MG}$, hybrid (internal combustion engine 14+MG 12) efficiency, acceleration, $A_{CC}$, etc.

In some embodiments, one or more of the sensors 52 may include their own processing capability to compute the results for additional information that can be provided to electronic control unit 50. In other embodiments, one or more sensors may be data-gathering-only sensors that provide only raw data to electronic control unit 50. In further embodiments, hybrid sensors may be included that provide a combination of raw data and processed data to electronic control unit 50. Sensors 52 may provide an analog output or a digital output.

Sensors 52 may be included to detect not only vehicle conditions but also to detect external conditions as well. Sensors that might be used to detect external conditions can include, for example, sonar, radar, lidar or other vehicle proximity sensors, and cameras or other image sensors. Image sensors can be used to detect, for example, traffic signs indicating a current speed limit, road curvature, obstacles, and so on. Still other sensors may include those that can detect road grade. While some sensors can be used to actively detect passive environmental objects, other sensors can be included and used to detect active objects such as those objects used to implement smart roadways that may actively transmit and/or receive data or other information.

Figure 2:
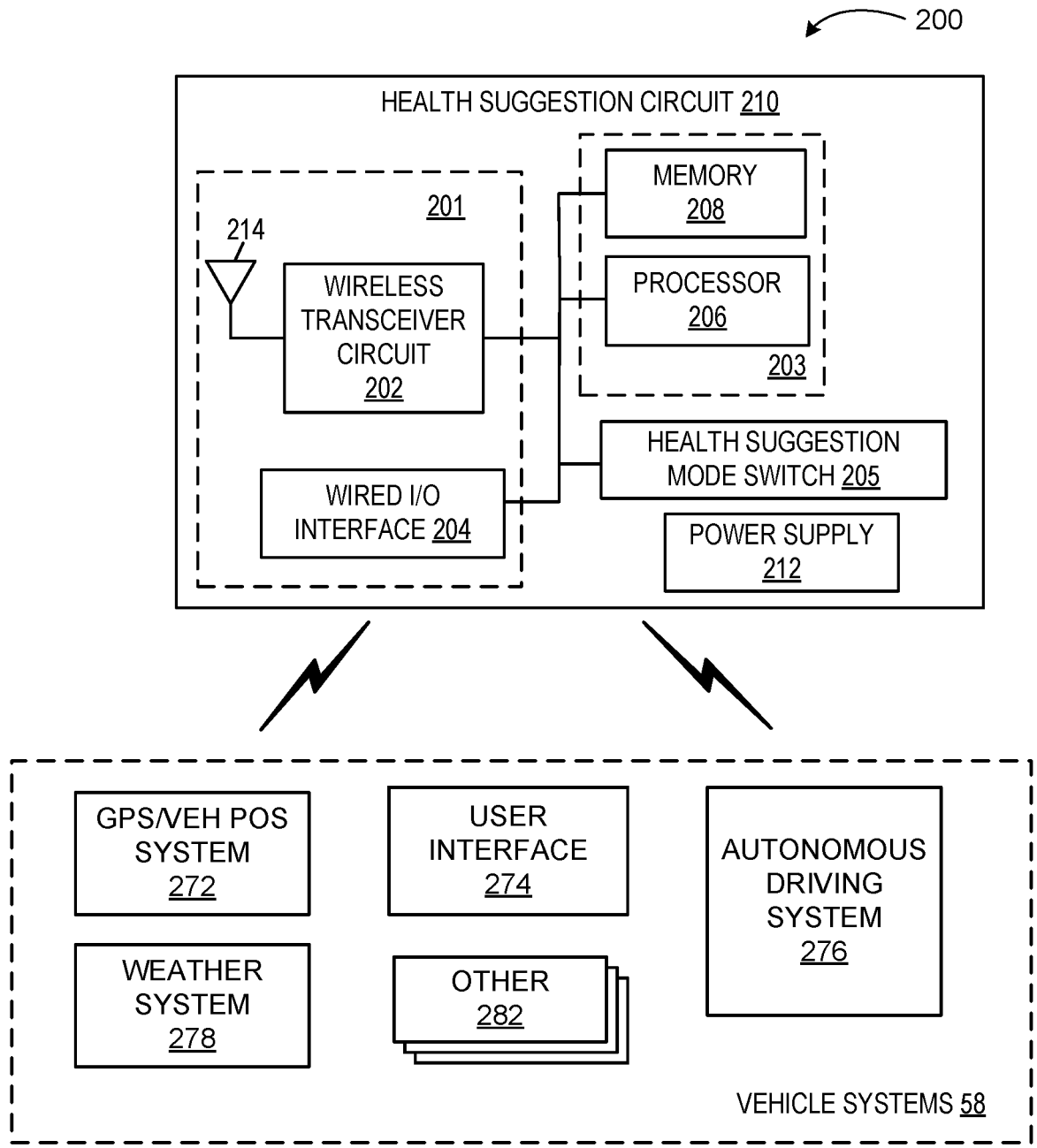
FIG. 2 illustrates an example architecture for automated activity suggestions based on wearable connectivity with vehicle systems according to embodiments of the disclosed technology.

FIG. 2 illustrates an example architecture for automated activity suggestions based on wearable connectivity with vehicle systems in accordance with one embodiment of the systems and methods described herein. Referring now to FIG. 2, in this example, health mode system 200 includes an health suggestion circuit 210, and a plurality of vehicle systems 58. Vehicle systems 58 can communicate with health suggestion circuit 210 via a wired or wireless communication interface. Although vehicle systems 58 are depicted as communicating with health suggestion circuit 210, they can also communicate with each other as well as with other vehicle systems. Health suggestion circuit 210 can be implemented as an ECU or as part of an ECU such as, for example electronic control unit 50. In other embodiments, health suggestion circuit 210 can be implemented independently of the ECU.

Health suggestion circuit 210 in this example includes a communication circuit 201, a decision circuit 203 (including a processor 206 and memory 208 in this example) and a power supply 212. Components of health suggestion circuit 210 are illustrated as communicating with each other via a data bus, although other communication in interfaces can be included. Health suggestion circuit 210 in this example also includes a health suggestion mode switch 205 that can be operated by the user to manually select the health suggestion mode.

Processor 206 can include a GPU, CPU, microprocessor, or any other suitable processing system. The memory 208 may include one or more various forms of memory or data storage (e.g., flash, RAM, etc.) that may be used to store the calibration parameters, images (analysis or historic), point parameters, instructions and variables for processor 206 as well as any other suitable information. Memory 208, can be made up of one or more modules of one or more different types of memory, and may be configured to store data and other information as well as operational instructions that may be used by the processor 206 to health suggestion circuit 210.

Although the example of FIG. 2 is illustrated using processor and memory circuitry, as described below with reference to circuits disclosed herein, decision circuit 203 can be implemented utilizing any form of circuitry including, for example, hardware, software, or a combination thereof. By way of further example, one or more processors, controllers, ASICs, PLAs, PALs, CPLDs, FPGAs, logical components, software routines or other mechanisms might be implemented to make up a health suggestion circuit 210.

Communication circuit 201 either or both a wireless transceiver circuit 202 with an associated antenna 214 and a wired I/O interface 204 with an associated hardwired data port (not illustrated). As this example illustrates, communications with health suggestion circuit 210 can include either or both wired and wireless communications circuits 201. Wireless transceiver circuit 202 can include a transmitter and a receiver (not shown) to allow wireless communications via any of a number of communication protocols such as, for example, WiFi, Bluetooth, near field communications (NFC), Zigbee, and any of a number of other wireless communication protocols whether standardized, proprietary, open, point-to-point, networked or otherwise. Antenna 214 is coupled to wireless transceiver circuit 202 and is used by wireless transceiver circuit 202 to transmit radio signals wirelessly to wireless equipment with which it is connected and to receive radio signals as well. These RF signals can include information of almost any sort that is sent or received by health suggestion circuit 210 to/from other entities such as sensors 52 and vehicle systems 58.

Wired I/O interface 204 can include a transmitter and a receiver (not shown) for hardwired communications with other devices. For example, wired I/O interface 204 can provide a hardwired interface to other components, including sensors 52 and vehicle systems 58. Wired I/O interface 204 can communicate with other devices using Ethernet or any of a number of other wired communication protocols whether standardized, proprietary, open, point-to-point, networked or otherwise.

Power supply 212 can include one or more of a battery or batteries (such as, e.g., Li-ion, Li-Polymer, NiMH, NiCd, NiZn, and $NiH_2$, to name a few, whether rechargeable or primary batteries), a power connector (e.g., to connect to vehicle supplied power, etc.), an energy harvester (e.g., solar cells, piezoelectric system, etc.), or it can include any other suitable power supply.

During operation, health suggestion circuit 210 can receive information from various vehicle sensors to determine whether the health suggestion mode should be activated. Also, the driver may manually activate the health suggestion mode by operating health suggestion mode switch 205. Communication circuit 201 can be used to transmit and receive information between health suggestion circuit 210 and sensors 52, and health suggestion circuit 210 and vehicle systems 58. Also, sensors 52 may communicate with vehicle systems 58 directly or indirectly (e.g., via communication circuit 201 or otherwise).

In various embodiments, communication circuit 201 can be configured to receive data and other information from sensors 52 that is used in determining whether to activate the health suggestion mode. Additionally, communication circuit 201 can be used to send an activation signal or other activation information to various vehicle systems 58 as part of entering the health suggestion mode. For example, as described in more detail below, communication circuit 201 can be used to send signals to, for example, one or more of: the vehicle positioning system 272, the user interface 274, the autonomous driving system 276, the weather system 278, and other systems 282. Examples of this are described in more detail below.

Figure 3:
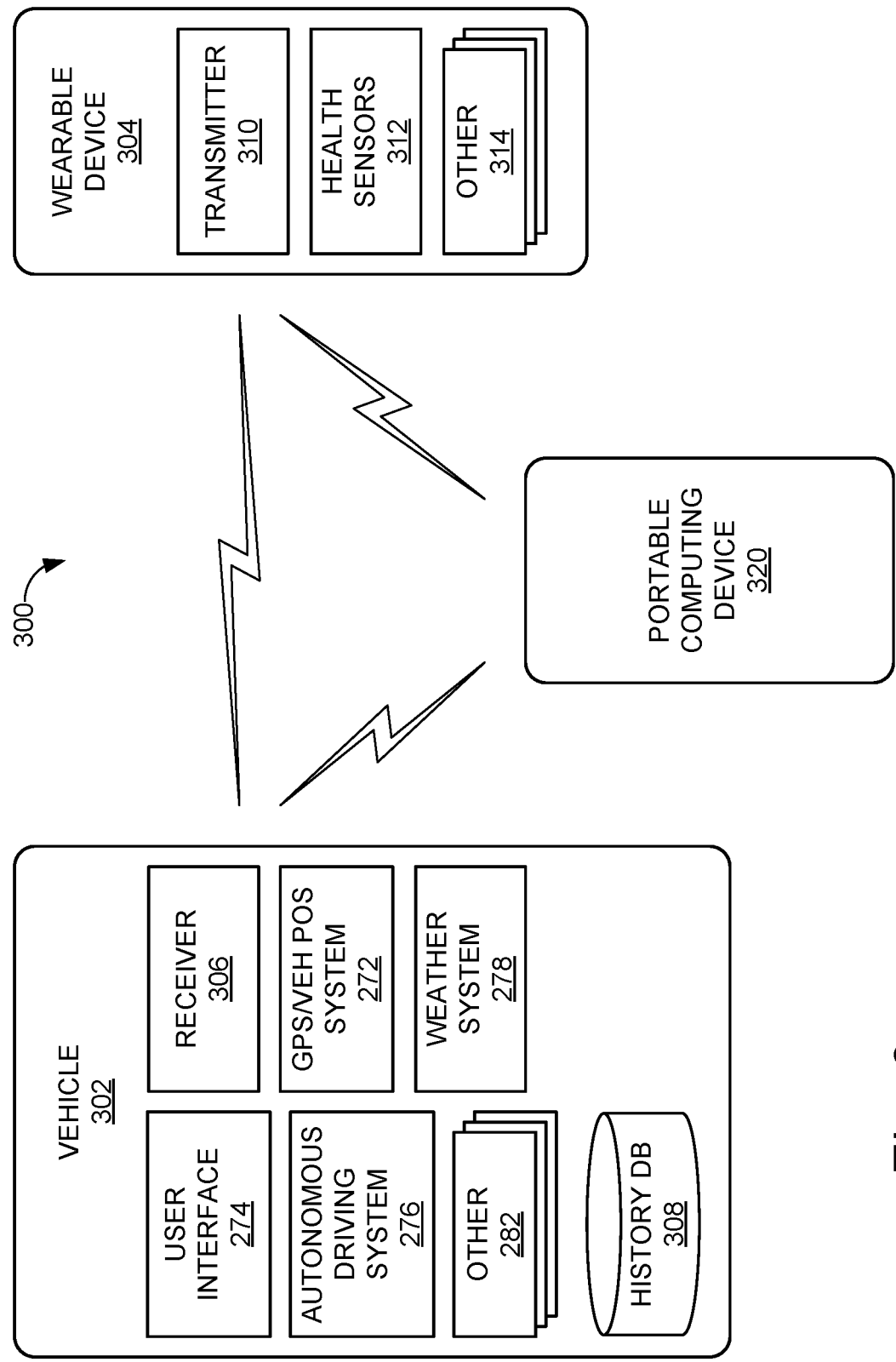
FIG. 3 illustrates a system for a vehicle to provide automated activity suggestions based on wearable connectivity with vehicle systems according to embodiments of the disclosed technology.

FIG. 3 illustrates a system 300 for a vehicle to provide automated activity suggestions based on wearable connectivity with vehicle systems according to embodiments of the disclosed technology. Referring to FIG. 3, the system 300 includes a vehicle 302 and communication with a wearable devices 304. In some embodiments, the vehicle 302 communicates directly with the wearable device 304. In other embodiments, the vehicle 302 communicates with a portable computing device 320, such as a smart phone or the like, which is in communication with the wearable device 304. The communications may be wired or wireless, and for example may employ a wireless communication technology such as Bluetooth, Wi-Fi, or the like.

The vehicle 302 may include elements of the health mode system 200 of FIG. 2. For example, the vehicle 302 may include the vehicle positioning system 272, the user interface 274, the autonomous driving system 276, the weather system 278, and other systems 282. In addition, referring again to FIG. 3, the vehicle 302 may include a receiver 306 for communicating with the wearable device 304 and/or the portable computing device 320. In some embodiments, the vehicle 302 may maintain a history database (DB) 308 to store a history of the activities in engaged in by a wearer of the wearable device 304.

FIG. 3 depicts only one wearable device 304. However, it should be understood that the vehicle 302 may communicate with multiple wearable devices 304, which may be worn by multiple occupants of the vehicle. Furthermore, the history database 308 may store histories of activities of these multiple occupants.

The wearable device 304 may include one or more health sensors 312. The health sensors 312 may include any health sensors, for example including heart rate monitors, step counters, the monitors, and the like. The health sensors 312 may collect health data from a wearer of the wearable device 304 using the health sensors 312. The wearable device 304 may include a transmitter 310 to send the collected health data to the vehicle 302, either directly or via the portable computing device 320. The wearable device 304 may include other systems 314 as well.

Figure 4:
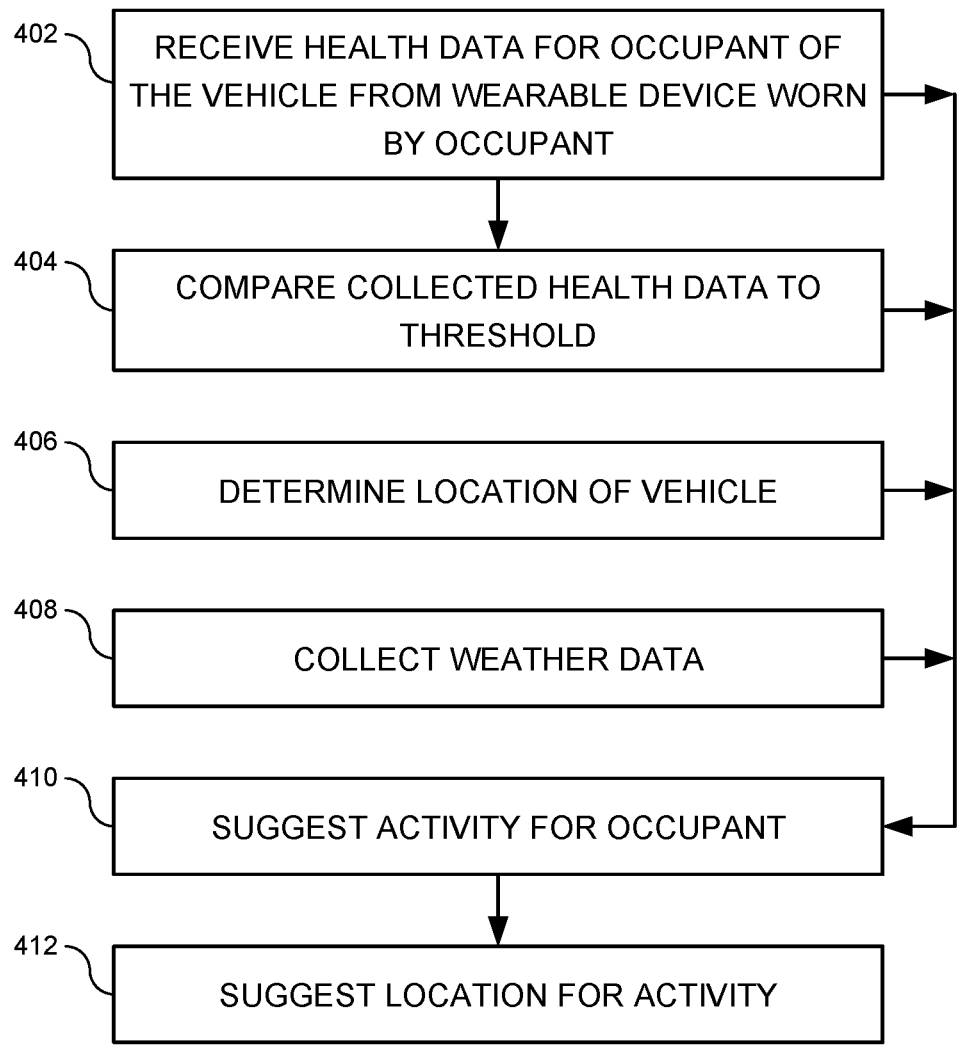
FIG. 4 illustrates elements of processes that may be performed by the vehicle 302 of FIG. 3 according to some embodiments of the disclosed technology.

FIG. 4 illustrates elements of processes 400 that may be performed by the vehicle 302 of FIG. 3 according to some embodiments of the disclosed technology. In various embodiments, one or more of the illustrated elements may be omitted, performed in sequences other than those described, and the like. In some embodiments, one or more of the elements may be performed, or partially performed, by the portable computing device 320 of FIG. 3.

Referring again to FIG. 4, the vehicle 302 may receive health data for an occupant of the vehicle 302, at 402. The health data may be collected by a wearable device 304 worn by the occupant. The vehicle 302 may receive the help data directly from the wearable devices 304, or indirectly through one or more other devices such as the portable computing device 320 of FIG. 3.

In some embodiments, the vehicle 302 may compare the collected health data to a threshold, at 404, for example as described above. As another example, the threshold may represent a maximum body temperature for the occupant, and the health data may represent a current body temperature of the occupant. In this example, the vehicle may compare the current body temperature to the maximum body temperature as part of the processes 400.

In some embodiments, one or more of the processes 400 may include determining a location of the vehicle 302, at 406. In some embodiments, the vehicle 302 may employ the vehicle positioning system 272 to determine the location of the vehicle 302. In other embodiments, the location may be determined by another device, for example such as the portable computing device 320. For example, the position may be determined using a global positioning system (GPS) or the like.

In some embodiments, one or more of the processes 400 may include collecting weather data, at 408. In some embodiments, the vehicle 302 may employ its weather system 278 to collect the weather data. In other embodiments, the weather data may be collected by another device, for example such as the portable computing device 320. For example, the weather data may be collected using a weather app or the like. The weather data may include current conditions, weather forecasts, and the like. The weather data may pertain to a current location, or future location, of the vehicle 302. Future locations of the vehicle 302 may be obtained using navigation systems, map programs, information supplied by occupants of the vehicle, and the like.

Based on various combinations of the above-described information obtained by the vehicle 302, the vehicle 302 may suggest an activity for the wearer of the wearable device 304, at 410. The suggested activity may include any activity, for example as described above, and in the examples that follow, without limitation. In some embodiments, when suggesting an activity, the vehicle 302 may also suggest a location for the activity, at 412. For example, when suggesting the wearer take a walk, the vehicle 302 may also suggest one or more locations for the walk.

Figure 5:
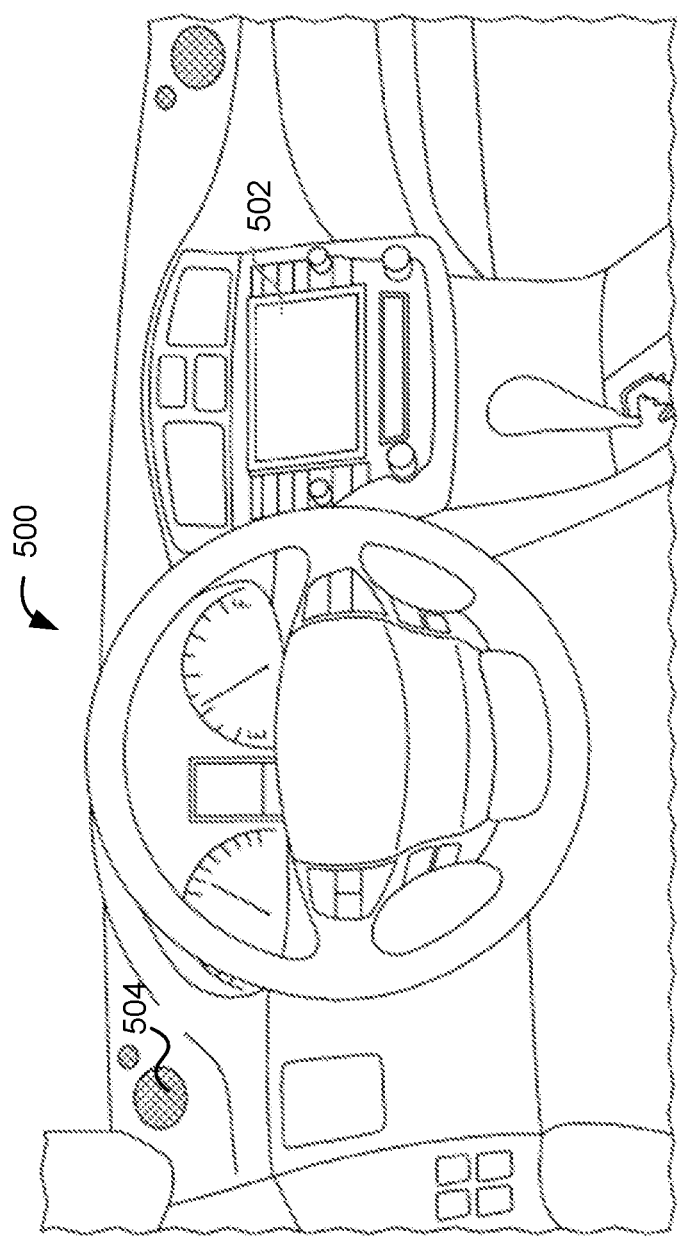
FIG. 5 illustrates an example vehicle user interface according to some embodiments of the disclosed technology.
Figure 6:
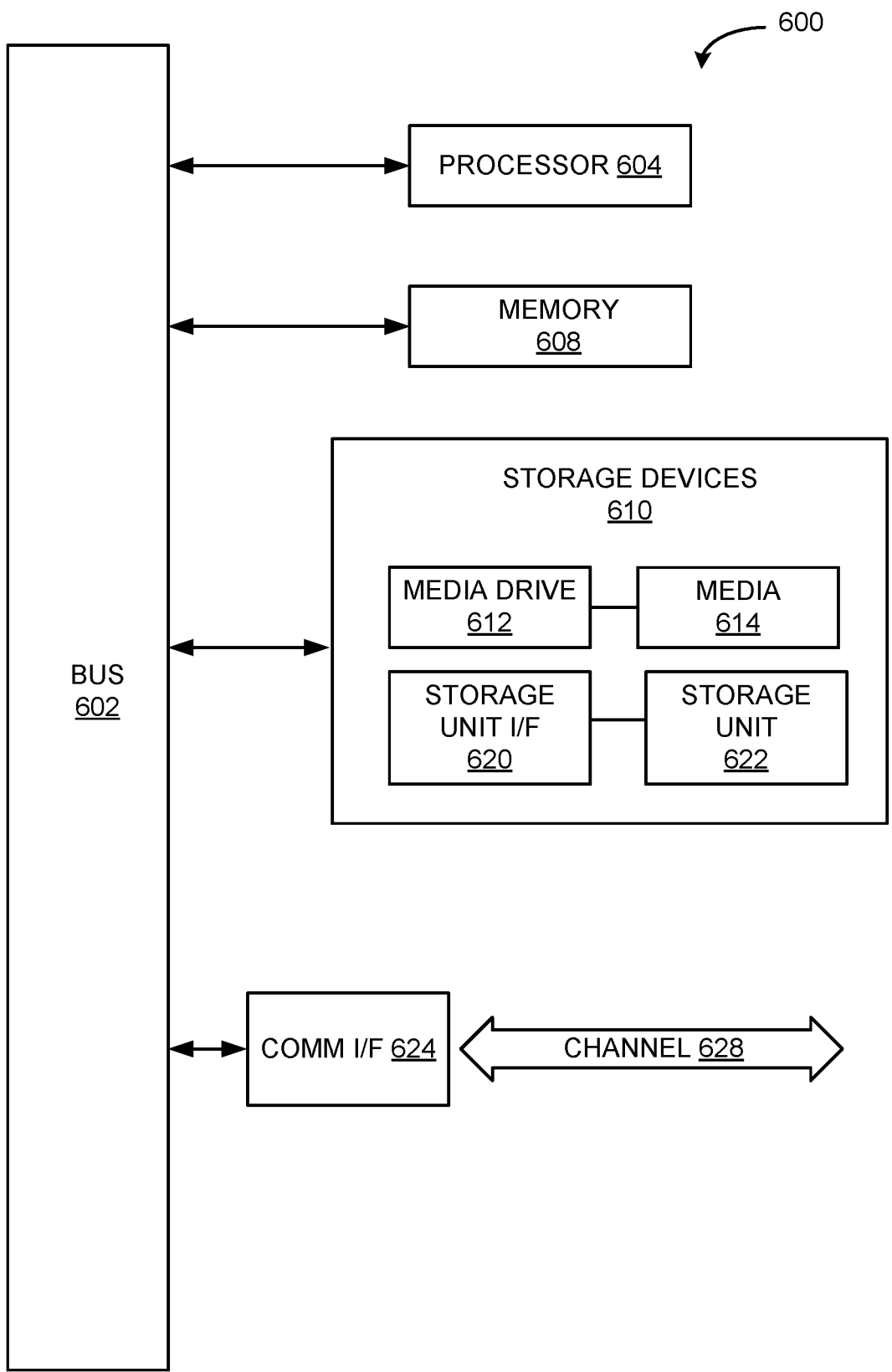
FIG. 6 is an example computing component that may be used to implement various features of embodiments described in the present disclosure.

The activity suggestion, and location if included, may be provided to the wearer in many ways. For example, the vehicle 302 may provide the activity suggestion through the user interface 274 of the vehicle 302. FIG. 5 illustrates an example vehicle user interface 500 according to some embodiments of the disclosed technology. Referring to FIG. 5, a portion of an automobile cabin is shown. The cabin may include a display panel 502. The display panel 502 may display the activity suggestion, for example as a textual message. The display panel 502 may display multiple activity suggestions. In some embodiments, the occupant may operate an input device to select one or more of the activity suggestions, in order to obtain more information concerning the activity suggestion. For example, the display panel 502 may be a touchscreen, which the occupant may operate to select an activity suggestion. The additional information for the activity suggestion may include, for example, a location for the activity, a time of the activity, the name of the activity, and the like. The occupant may operate the input device to dismiss a suggestion, accept a suggestion, or the like. When the user accepts a suggested activity, the vehicle 302 may record the accepted activity in the history database 308 for use in future suggestions.

Referring again to FIG. 5, the cabin may include an audio system 504, which may include one or more speakers, one or more microphones, and the like. One or more of the speakers may announce the suggested activities. The speakers may also provide voice prompts that allow the occupants to interact with the vehicle 302, for example to accept activity suggestions, dismiss activity suggestions, get more activity suggestions, get more information concerning an activity suggestion, and the like.

In some embodiments, the vehicle 302 may provide the activity suggestions to the wearable device 304, either directly or through the portable computing device 320. In such embodiments, the wearable device 304 may include a user interface, for example including a display, a speaker, or the like. Responsive to receiving the activity suggestions, the wearable device 304 may provide those activity suggestions to the occupant using messages that are announced, displayed, or like.

In some embodiments, the vehicle 302 may provide the activity suggestions to the occupants using the portable computing device 320. In such embodiments, the portable computing device 320 may include a user interface, for example including a display, speaker, or like. Responsive to receiving the activity suggestions, the portable computing device 320 may provide those activity suggestions to the occupant using messages that are announced, displayed, or like.

Now several examples of the operation of the disclosed technology are described. In one example, the health data collected by the wearable device 304 may indicate that the wearer is experiencing stress. For example, the health data may include a heart rate of the wearer. The vehicle 302 may store a threshold heart rate for the wearer. In some examples, the threshold heart rate may be provided by the wearer. In other examples, the vehicle 302 may learn the threshold heart rate by observing the wearer's heart rate over a period of time. In other examples, the threshold heart rate may be provided by the wearable device 304, or by the portable computing device 320. The vehicle 302 may compare the current heart rate of the wearer to the wearer's threshold heart rate. When the current heart rate exceeds the threshold heart rate, the vehicle 302 may suggest an activity for the wearer.

The suggested activity may be based on the location of the vehicle 302. For example, when the vehicle 302 is located in an area where autonomous driving is permitted, the vehicle 302 may offer to engage the autonomous driving system 276 of the vehicle 302. Furthermore, the vehicle 302 may suggest a location for this activity. That is, the vehicle 302 may offer to navigate the vehicle over one or more particular routes. For example, the vehicle 302 may offer to take a scenic route having little traffic.

As another example, on detecting a heart rate exceeding the wearer's heart rate threshold, the vehicle 302 may suggest stopping the vehicle 302 so the wearer may enjoy a refreshment. The suggested activity may be based on the location of the vehicle 302. For example, the vehicle 302 may suggest stopping for refreshments at one or more restaurants in the vicinity of the vehicle 302.

in another example, the health data may indicate that the wearer of the wearable device 304 is hungry. For example, the health data may indicate a low blood sugar level. The vehicle 302 may store a blood sugar threshold for the wearer. When the current blood sugar level falls below the blood sugar threshold, the vehicle 302 may determine that the wearer of the wearable device 304 is hungry. Responsive to determining the wearer is hungry, the vehicle may suggest stopping the vehicle for a meal. The suggested activity may be based on the location of the vehicle 302. For example, the vehicle 302 may suggest one or more restaurants near the vehicle.

In another example, the wearer of the wearable device 304 may suffer from diabetes, and may use the wearable device 304 to monitor blood glucose levels. In this example, the vehicle 302 may store blood glucose thresholds for the wearer. When the vehicle 302 determines that the health data collected by the wearable device 304 indicates a blood glucose level exceeding the blood glucose thresholds for the wearer, the vehicle 302 may suggest insulin therapy. The vehicle 302 may also suggest a convenient location for the insulin therapy. For example, the vehicle 302 may direct the wearer to a nearby highway rest area, to a clinic, or the like.

In some examples, the vehicle 302 may determine an emergency situation exists based on the health data. For example, the health data collected by the wearable device 304 may include measurements of epidermal electrical activity. By comparing the activity with a stored threshold, the vehicle 302 may determine that the wearer is experiencing a seizure. In such an emergency, the vehicle 302 may suggest stopping the vehicle. For example, the vehicle 302 may suggest automatically stopping the vehicle in a safe place, for example such as a shoulder of a road on which the vehicle 302 is traveling. In some embodiments, the vehicle 302 may determine that the wearer of the wearable device 304 is the operator of the vehicle 302. In such embodiments, the vehicle 302 may proceed with implementing the suggestion without waiting for the wearer to confirm the suggestion. For example, when the vehicle 302 is located in an autonomous driving zone, the vehicle 302 may engage its autonomous driving system 276 to drive the wearer to a hospital emergency room for treatment.

As another example of an emergency situation, the vehicle 302 may determine that the wearer of the wearable device 304 is the operator of the vehicle 302, and the health data may indicate that the wearer of the wearable device 304 has fallen asleep. For example, the wearable device 304 may be implemented as a pair of eyeglasses, and may include a head tilt sensor, an eyes closed sensor, or the like. In such embodiments, the health data may indicate the wearer is asleep, for example because the wearer's eyes are closed, or the wearer's head is tilted downward. In this case, the vehicle 302 may suggest the wearer wake up, for example using a loud noise or the like. The vehicle 302 may further suggest stopping for a rest, and may suggest a nearby highway rest area. Of course, many other examples are contemplated.

As used herein, the terms circuit and component might describe a given unit of functionality that can be performed in accordance with one or more embodiments of the present application. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 5. Various embodiments are described in terms of this example-computing component 500. After reading this description, it will become apparent to a person skilled in the relevant art how to implement the application using other computing components or architectures.

Referring now to FIG. 5, computing component 500 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 500 might also represent computing capabilities embedded within or otherwise available to a given device. For example, a computing component might be found in other electronic devices such as, for example, portable computing devices, and other electronic devices that might include some form of processing capability.

Computing component 500 might include, for example, one or more processors, controllers, control components, or other processing devices. A processor 504 might be implemented using a general-purpose or special-purpose processing engine such as, for example, a microprocessor, controller, or other control logic. Processor 504 may be connected to a bus 502. However, any communication medium can be used to facilitate interaction with other components of computing component 500 or to communicate externally.

Computing component 500 might also include one or more memory components, simply referred to herein as main memory 508. For example, random access memory (RAM) or other dynamic memory, might be used for storing information and instructions to be executed by processor 504. Main memory 508 might also be used for storing temporary variables or other intermediate information during execution of instructions to be executed by processor 504. Computing component 500 might likewise include a read only memory ("ROM") or other static storage device coupled to bus 502 for storing static information and instructions for processor 504.

The computing component 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a solid-state drive, a magnetic tape drive, an optical drive, a compact disc (CD) or digital video disc (DVD) drive (R or RW), or other removable or fixed media drive might be provided. Storage media 514 might include, for example, a hard disk, an integrated circuit assembly, magnetic tape, cartridge, optical disk, a CD or DVD. Storage media 514 may be any other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing component 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory component) and memory slot. Other examples may include a PCMCIA slot and card, and other fixed or removable storage units 522 and interfaces 520 that allow software and data to be transferred from storage unit 522 to computing component 500.

Computing component 500 might also include a communications interface 524. Communications interface 524 might be used to allow software and data to be transferred between computing component 500 and external devices. Examples of communications interface 524 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 524 may be carried on signals, which can be electronic, electromagnetic (which includes optical) or other signals capable of being exchanged by a given communications interface 524. These signals might be provided to communications interface 524 via a channel 528. Channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 500 to perform features or functions of the present application as discussed herein.

It should be understood that the various features, aspects and functionality described in one or more of the individual embodiments are not limited in their applicability to the particular embodiment with which they are described. Instead, they can be applied, alone or in various combinations, to one or more other embodiments, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A vehicle, comprising:
 a hardware processor; and
 a non-transitory machine-readable storage medium encoded with instructions executable by the hardware processor to perform a method comprising:
  collecting health data for an occupant of the vehicle from a wearable device worn by the occupant;
  collecting weather data from a weather system communicatively coupled with the vehicle;
  determining a location of the vehicle; and
  suggesting an activity for the occupant based on the collected health data, the location of the vehicle, and the weather data, wherein the activity is determined to be an indoor activity or an outdoor activity based on the weather data.

2. The vehicle of claim 1, wherein the method further comprises:
 suggesting a second location for the activity.

3. The vehicle of claim 1, wherein the method further comprises:
 collecting a history of activities performed by the occupant; and
 suggesting the activity for the occupant based on the collected health data, the location of the vehicle, and the history of activities.

4. The vehicle of claim 1, wherein the method further comprises:
 comparing the collected health data to a threshold; and
 suggesting the activity for the occupant based on the collected health data and the threshold.

5. The vehicle of claim 1, wherein collecting the health data for the occupant of the vehicle from the wearable device worn by the occupant comprises:
 collecting the health data directly from the wearable device.

6. The vehicle of claim 1, wherein collecting the health data for the occupant of the vehicle from the wearable device worn by the occupant comprises:
 collecting the health data from a portable computing device in communication with the wearable device.

7. A non-transitory machine-readable storage medium encoded with instructions executable by a hardware processor to perform a method comprising:
 collecting health data for an occupant of a vehicle from a wearable device worn by the occupant;
 collecting weather data from a weather system communicatively coupled with the vehicle;
 determining a location of the vehicle; and
 suggesting an activity for the occupant based on the collected health data, the location of the vehicle, and the weather data, wherein the activity is determined to be an indoor activity or an outdoor activity based on the weather data.

8. The vehicle of claim 1, wherein the weather data comprises current conditions and weather forecasts.

9. The vehicle of claim 1, wherein the weather system determines the weather data associated with a future location of the vehicle, wherein the future location is obtained using a navigation system communicatively coupled with the vehicle.

10. The medium of claim 7, wherein the method further comprises:
 suggesting a second location for the activity.

11. The medium of claim 7, wherein the method further comprises:
 collecting a history of activities performed by the occupant; and
 suggesting the activity for the occupant based on the collected health data, the location of the vehicle, and the history of activities.

12. The medium of claim 7, wherein the method further comprises:
 comparing the collected health data to a threshold; and
 suggesting the activity for the occupant based on the collected health data and the threshold.

13. The medium of claim 7, wherein collecting the health data for the occupant of the vehicle from the wearable device worn by the occupant comprises:
 collecting the health data directly from the wearable device.

14. The medium of claim 7, wherein collecting the health data for the occupant of the vehicle from the wearable device worn by the occupant comprises:
 collecting the health data from a portable computing device in communication with the wearable device.

15. A method for a vehicle, the method comprising:
 collecting health data for an occupant of the vehicle from a wearable device worn by the occupant;
 collecting weather data from a weather system communicatively coupled with the vehicle;
 determining a location of the vehicle; and
 suggesting an activity for the occupant based on the collected health data, the location of the vehicle, and the weather data, wherein the activity is determined to be an indoor activity or an outdoor activity based on the weather data.

16. The method of claim 15, further comprising:
 suggesting a second location for the activity.

17. The method of claim 15, further comprising:
 collecting a history of activities performed by the occupant; and
 suggesting the activity for the occupant based on the collected health data, the location of the vehicle, and the history of activities.

18. The method of claim 15, further comprising:
 comparing the collected health data to a threshold; and
 suggesting the activity for the occupant based on the collected health data and the threshold.

19. The method of claim 15, wherein collecting the health data for the occupant of the vehicle from the wearable device worn by the occupant comprises:
 collecting the health data directly from the wearable device.

* * * * *